United States Patent [19]
Myers

[11] Patent Number: 5,336,235
[45] Date of Patent: Aug. 9, 1994

[54] KERATOME

[76] Inventor: William D. Myers, 5855 Wingcroft Ct., Birmingham, Mich. 48010

[21] Appl. No.: 734,675

[22] Filed: Jul. 23, 1991

[51] Int. Cl.⁵ .............................................. A61B 17/32
[52] U.S. Cl. .................................................... 606/166
[58] Field of Search ................ 606/167, 166, 131, 132

[56] References Cited

U.S. PATENT DOCUMENTS 3,886,943  6/1975  Skiff et al. ...................... 606/167 X
3,929,138  12/1975  Curi ..................................... 606/167

FOREIGN PATENT DOCUMENTS 8602257  4/1986  PCT Int'l Appl. ................. 606/166

*Primary Examiner*—Michael H. Thaler
*Attorney, Agent, or Firm*—Gifford, Groh, Sprinkle, Patmore and Anderson

[57] ABSTRACT

A keratome is disclosed for use in eye surgery. The keratome includes an elongated handle having two ends. A blade is secured to one end of the handle so that the blade has a cutting edge spaced from and facing outwardly from the end of the handle. The blade is curvilinear in shape and has a radius of curvature substantially the same as the radius of curvature of the eye immediately adjacent the outer periphery of the cornea of the eye.

4 Claims, 1 Drawing Sheet

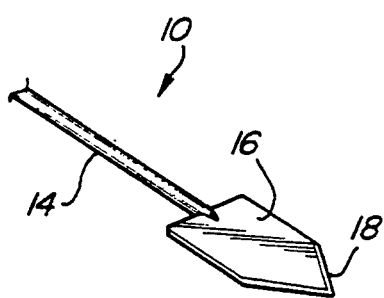
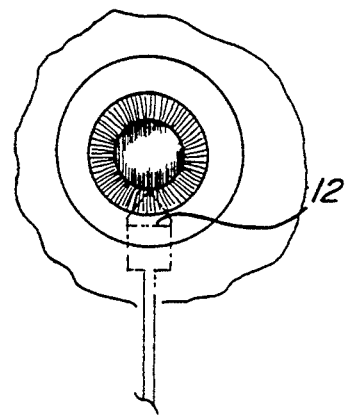
Fig-1 PRIOR ART
Fig-2 PRIOR ART
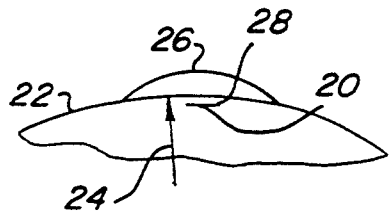
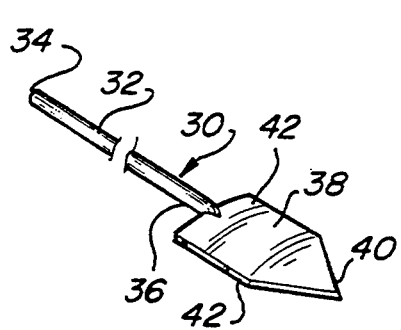
Fig-3 PRIOR ART
Fig-4
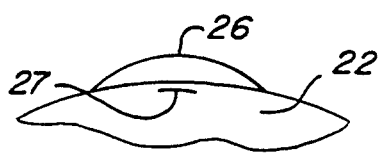
Fig-5
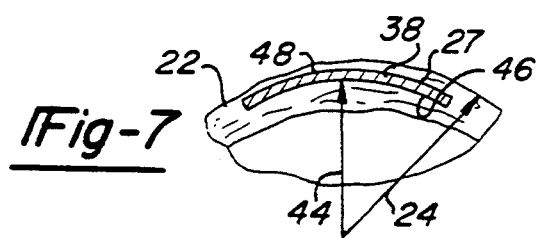
Fig-7
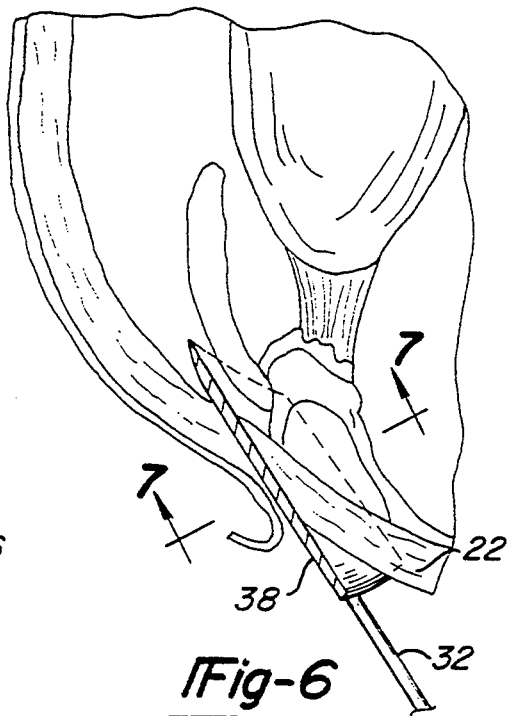
Fig-6 ically the same as the radius of curvature of the sclera in the area immediately adjacent the cornea. As such, the entire blade is evenly spaced under the outer surface of the sclera thereby reducing the possibility of cutting through the outer surface of the sclera along the sides of the sclera tunnel.

KERATOME

BACKGROUND OF THE INVENTION

I. Field of the Invention

The present invention relates generally to surgical instruments and, more particularly, to a keratome for use in eye surgery.

II. Description of the Prior Art

In cataract surgery, it is necessary to first remove the opacified lens from the human eye. Thereafter, the natural lens is typically replaced by an artificial lens which restores vision to the patient.

In cataract surgery, a sclera dissector is first utilized to form a small tunnel in the sclera at a position spaced a few millimeters outwardly from the cornea of the eye. In doing so, the scleral dissector forms a small flap in the sclera.

After the tunnel is formed in the sclera, a small keratome is first used to complete the incision within the tunnel and into the anterior chamber of the eye. Where the natural lens of the eye is removed by phacoemulsification, a keratome having a width of approximately three millimeters completes the incision under the sclera flap and into the anterior chamber of the eye. This relatively small incision is sufficient to permit the insertion of the phacoemulsifier into the eye in order to remove the natural lens of the eye. Following removal of the natural lens of the eye, the phacoemulsifier is likewise removed from the eye.

In order to thereafter implant an artificial lens into the eye, it is necessary to widen the incision in the eye to a width of 4.0 millimeters or more in order to implant the lens.

With reference now to FIGS. 1-3, in order to widen the incision to permit the implantation of the artificial lens, it has been the previously known practice to use a keratome 10 having a width of 4.0 millimeters or more which is inserted into the sclera tunnel 12 (FIG. 2) and into the anterior chamber of the eye.

These previously known keratomes 10 typically comprise an elongated handle 14 having a flat blade 16 at one end. A generally V-shaped cutting edge 18 faces away from the handle 14 and cuts through the sclera under the cornea as the keratome 10 is inserted through the scleral tunnel 12 and into the anterior chamber of the eye.

One disadvantage off these previously known keratomes 10, however, is that the blade 16 is planar in shape. As such, as shown in FIG. 3, the blade creates a flat cut 20 in the sclera 22. The sclera 22, however, is curved as indicated by the radius of curvature 24 of the eye in the area immediately adjacent the cornea 26 so that the thickness of the sclera at the center of the blade cut is larger than the thickness of the sclera along the sides of the blade cut. Consequently, when the keratomes 10 having relatively wide blades 16 are used to perform the final incision into the eye, it is possible for the side edges of the keratome blade 16 to protrude through and cut the top surface of the sclera 22 due to the interference created between the curved sclera 22 and the flat blade 16 of the keratome 10.

SUMMARY OF THE PRESENT INVENTION

The present invention provides a keratome which overcomes all of the above mentioned disadvantages of the previously known devices.

In brief, the keratome of the present invention comprises an elongated handle having two ends. A blade is secured to one end of the handle and the blade has a cutting edge which is spaced from and faces outwardly from the end of the handle.

Unlike the previously known keratomes, the keratome blade of the present invention is curvilinear in shape when viewed along a plane substantially perpendicular to the plane of the blade This curvilinear shape of the keratome has a radius of curvature substantially the same as the radius of curvature of the sclera in the area immediately adjacent the cornea. As such, the entire blade is evenly spaced under the outer surface of the sclera thereby reducing the possibility of cutting through the outer surface of the sclera along the sides of the sclera tunnel.

BRIEF DESCRIPTION OF THE DRAWING

A better understanding of the present invention will be had upon reference to the following detailed description when read in conjunction with the accompanying drawings, wherein like reference characters refer to like parts throughout the several views, and in which:

FIG. 1 is an elevational view of a prior art keratome;

FIG. 2 is a plan view illustrating the use of the prior art keratome;

FIG. 3 is a side view illustrating the incision made by a prior art keratome;

FIG. 4 is an elevational view of the preferred embodiment of the present invention;

FIG. 5 is a side view illustrating the incision created by a keratome according to the present invention;

FIG. 6 is a diagrammatic view illustrating the operation of the keratome of the present invention; and FIG. 7 is a sectional view taken substantially along line 7—7 in FIG. 6.

DETAILED DESCRIPTION OF A PREFERRED EMBODIMENT OF THE PRESENT INVENTION

With reference first to FIG. 4, a preferred embodiment of the keratome 30 of the present invention is thereshown. The keratome 30 includes an elongated handle 32 having two ends 34 and 36. A blade 38 is secured to one end 36 of the handle 32.

Referring now to FIGS. 4, 6 and 7, the keratome blade 38 has a cutting edge 40 which is spaced from and faces outwardly from the end 36 of the handle 32. Moreover, as best shown in FIG. 4, the cutting edge 40 when viewed in plan is generally V-shaped and terminates into generally parallel side edges 42.

As is best shown in FIGS. 6 and 7, the keratome blade 38 is thin-walled and curvilinear in shape along a plane perpendicular to the blade 38 as best shown in FIG. 7. As such, the blade 38 has both a concave cylindrical inner surface 46 and a convex cylindrical outer surface 48. Furthermore, as best shown in FIG. 7, the radius of curvature 44 of the blade 38 is substantially the same as the radius of curvature 24 of the sclera 22 immediately adjacent the cornea of the eye.

In operation, the keratome 30 of the present invention is inserted into the sclera tunnel as shown in both FIGS. 6 and 7. Due to the curvilinear shade of the keratome blade 38, a curvilinear incision 27 (FIG. 5) is formed in the sclera 22 and the thickness of the sclera 22 between the blade 38 and the outer surface of the sclera remains substantially constant as the keratome blade 38 is inserted into the sclera tunnel. Consequently, the keratome 30 minimizes the possibility of the side edges of the keratome blade 38 cutting through the top surface of the sclera as in the previously known devices.

Having described my invention, many modifications thereto will become apparent to those skilled in the art to which it pertains without deviation from the spirit of the invention as defined by the scope of the appended claims.

I claim:

1. A keratome for use in eye surgery, said keratome comprising:

an elongated handle having a longitudinal axis and two ends, a blade secured to one end of said handle, said blade having a left side edge, a right side edge and a thin walled body portion extending between said left side edge and said right side edge, said blade having a cutting edge spaced from and facing away from said one end of said handle, said cutting edge extending between said left side edge and said right side edge, said blade being curvilinear in shape along a plane substantially perpendicular to said blade so that said blade has a concave inner surface and a cylindrical convex outer surface, said blade having a radius of curvature about an axis substantially parallel to said longitudinal axis of said handle.

2. The invention as defined in claim 1 wherein said radius of curvature of said blade is substantially the same as a radius of curvature of a human eye adjacent an outer periphery of the cornea of the eye.

3. The invention as defined in claim 1 wherein said cutting edge of said blade is V-shaped, and wherein said left side edge and said right side edge extend from opposite sides of the cutting edge.

4. The invention as defined in claim 3 wherein said side edges extend in a direction substantially parallel to said longitudinal axis of said handle.

* * * * *

UNITED STATES PATENT AND TRADEMARK OFFICE
CERTIFICATE OF CORRECTION

PATENT NO. : 5,336,235
DATED : August 9, 1994
INVENTOR(S) : William D. Myers

It is certified that error appears in the above-indentified patent and that said Letters Patent is hereby corrected as shown below:

Column 1, line 19, "sclera" should be --scleral--.

Column 1, line 24, "sclera" should be --scleral--.

Column 1, line 39, "sclera" should be --scleral--.

Column 1, line 48, "off" should be --of--.

Column 2, line 9, insert --.-- after "blade".

Column 2, line 16, "sclera" should be --scleral--.

Column 2, line 59, "sclera" should be --scleral--.

Column 2, line 60, "shade" should be --shape--.

Column 2, line 67, "sclera" should be --scleral--.

Signed and Sealed this

Twenty-ninth Day of November, 1994

Attest:

BRUCE LEHMAN

*Attesting Officer*     *Commissioner of Patents and Trademarks*